US009881767B2

(12) United States Patent
Kuwahara et al.

(10) Patent No.: US 9,881,767 B2
(45) Date of Patent: Jan. 30, 2018

(54) COHERENCE MEASURING DEVICE FOR SPIN-POLARIZED ELECTRON BEAM AND METHOD USING THE SAME

(71) Applicant: NATIONAL UNIVERSITY CORPORATION NAGOYA UNIVERSITY, Nagoya-shi, Aichi (JP)

(72) Inventors: Makoto Kuwahara, Nagoya (JP); Nobuo Tanaka, Nagoya (JP); Toru Ujihara, Nagoya (JP); Koh Saitoh, Nagoya (JP)

(73) Assignee: NATIONAL UNIVERSITY CORPORATION NAGOYA UNIVERSITY, Nagoya (JP)

( * ) Notice: Subject to any disclaimer, the term of this patent is extended or adjusted under 35 U.S.C. 154(b) by 0 days.

(21) Appl. No.: 15/516,976

(22) PCT Filed: Sep. 28, 2015

(86) PCT No.: PCT/JP2015/077393
§ 371 (c)(1),
(2) Date: Apr. 5, 2017

(87) PCT Pub. No.: WO2016/056425
PCT Pub. Date: Apr. 14, 2016

(65) Prior Publication Data
US 2017/0309446 A1   Oct. 26, 2017

(30) Foreign Application Priority Data
Oct. 9, 2014   (JP) .................. 2014-208345

(51) Int. Cl.
*H01J 37/26*   (2006.01)

(52) U.S. Cl.
CPC ..... *H01J 37/26* (2013.01); *H01J 2237/24557* (2013.01)

(58) Field of Classification Search
CPC ................ H01J 37/26; H01J 2237/24557
See application file for complete search history.

(56) References Cited

U.S. PATENT DOCUMENTS

| 2008/0210868 A1 | 9/2008 | Kohashi et al. |
| 2013/0009058 A1 | 1/2013 | Tanaka et al. |

FOREIGN PATENT DOCUMENTS

| JP | H10-106465 A | 4/1998 |
| JP | 2007-258119 A | 10/2007 |

(Continued)

OTHER PUBLICATIONS

Nitta et al., "Spin-interference device," Applied Physics Letters, Aug. 2, 1999, vol. 75, No. 5, pp. 695-697.

(Continued)

*Primary Examiner* — Mark R Gaworecki
(74) *Attorney, Agent, or Firm* — Oliff PLC

(57) ABSTRACT

A path of a spin-polarized electron beam is split into two by a splitter. A spin direction of the spin-polarized electron beam is rotated by a spin direction rotator disposed on a first path, and delayed by a first delay device. On a second path, the electron beam passes through a sample stage. The spin-polarized electron beams split into the first path and the second path are superposed by a biprism, and its intensity distribution is measured. Coherence is measured from a relation between a spin direction rotation angle, a delay time, and a visibility of an interference fringe.

13 Claims, 2 Drawing Sheets

(56) References Cited

FOREIGN PATENT DOCUMENTS

| JP | 2008-218063 A | 9/2008 | | |
|---|---|---|---|---|
| JP | WO 2011122171 A1 | * | 10/2011 | ............ H01J 37/073 |
| WO | 2011/122171 A1 | | 10/2011 | |

OTHER PUBLICATIONS

Kato et al., "Observation of the Spin Hall Effect in Semiconductors," Science, Dec. 10, 2004, vol. 306, pp. 1910-1913.
Kusunoki et al., "Spatial coherence of electron beam in spin-polarized transmission electron microscope," Meeting Abstracts of the Physical Society of Japan, 2013, vol. 68, No. 2, p. 858.
Kuwahara et al., "Development of Spin-Polarized and Pulsed Transmission Electron Microscope—Based on the Fundamentals and the Advantage of Polarized Electron Source," Kenbikyo, 2013, vol. 48, No. 1, pp. 3-8.
Dec. 15, 2015 International Search Report issued in International Patent Application No. PCT/JP2015/077393.
Dec. 15, 2015 Written Opinion issued in International Patent Application No. PCT/JP2015/077393.

\* cited by examiner

COHERENCE MEASURING DEVICE FOR SPIN-POLARIZED ELECTRON BEAM AND METHOD USING THE SAME The present teachings disclose a measuring device that measures coherence (coherence length and/or coherence time) for an electron beam having high spin polarization. The present teachings further disclose a method of measuring a characteristic of a sample using the measuring device.

BACKGROUND ART

The inventors of the present teachings developed a semiconductor photocathode including a distorted superlattice semiconductor layer, and succeeded in generating an electron beam having high spin polarization (referring for example to an electron beam with a majority of its electrons being in up-spin, or an electron beam with a majority of its electrons being in down-spin, which are called spin-polarized electron beam herein).

SUMMARY OF INVENTION

Technical Problem

Measurement of the coherence of the spin-polarized electron beam enables various kinds of measurements. For example, if a phenomenon in which the coherence of the spin-polarized electron beam changes when the beam passes through a sample can be observed, a characteristic of the sample can be identified by clarifying interaction between the sample and the spin-polarized electron beam. This in turn enables evaluation of a state of spin in the sample, which is very useful in the technical fields, such as quantum computers and spintronics. However, there is currently no practical method for measuring the coherence of the spin-polarized electron beam.

The present teachings propose a device of measuring coherence of a spin-polarized electron beam and a method of using the device.

Solution to Technical Problem

A coherence measuring device disclosed herein may comprise: a splitter configured to split a path of a spin-polarized electron beam into two paths; a spin direction rotator and a first delay device that are disposed on one of the split two paths (first path) split by the splitter; a sample stage disposed on another of the two paths (second path) split by the splitter; a biprism that superposes spin-polarized electron beams split into the first path and the second path; and an intensity distribution measuring device configured to measure an intensity distribution of the superposed spin-polarized electron beams. By disposing a sample on the sample stage, interaction between the sample and the spin-polarized electron beam can be measured. A second delay device may further be disposed on the second path, as needed.

An interference fringe is generated by splitting the spin-polarized electron beam into two paths, and superposing the two split beams. A visibility of the interference fringe changes as follows.

(1) By using the first delay device and the second delay device, a time relation between the spin-polarized electron beam from the first path and the spin-polarized electron beam from the second path can be adjusted. A time difference can be adjusted in a range from a state where the spin-polarized electron beam from the first path travels earlier than the spin-polarized electron beam from the second path and a state where the spin-polarized electron beam from the first path travels later than the spin-polarized electron beam from the second path. The visibility of the interference fringe is greatest at a specific time difference (difference between delay time by the first delay device and delay time by the second delay device). The visibility of the interference fringe is maintained before and after the specific time difference, and the interference fringe is no longer measured when the time difference deviates from the specific time difference by a coherence time or longer. The coherence time can be measured from a time difference at which the visibility of the interference fringe deteriorates and the specific time difference as aforementioned. A coherence length can be identified by multiplying the coherence time by a traveling speed of the electron beam.

(2) The spin direction of the spin-polarized electron beam traveling on the first path is rotated by the spin direction rotator. The spin direction of the spin-polarized electron beam traveling on the second path may be changed by an interaction with a sample. Due to this, the visibility of the interference fringe is greatest in a state where a rotation angle by the spin direction rotator is adjusted to a specific rotation angle. The visibility of the interference fringe decreases as the rotation angle deviates away therefrom in either increasing or decreasing trend. By observing a phenomenon where the visibility of the interference fringe changes depending on the rotation angle by the spin direction rotator, it can be confirmed that what is being observed is an interference fringe obtained by the spin-polarized electron beam.

(3) An angle by which the spin direction is rotated by the interaction with the sample can be measured based on the rotation angle with which the visibility of the interference fringe is the greatest.

(4) A ratio of electrons of which spin directions are inverted by the interaction with the sample can be measured based on an intensity of the interference fringe with which the visibility of the interference fringe is the greatest.

(5) As will be described below, no sample needs to be disposed on the sample stage when the coherence of the spin-polarized electron beam is measured. The sample stage itself is configured to be transparent to the spin-polarized electron beam.

(6) When the coherence of the spin-polarized electron beam is to be measured, a state in which the spin-polarized electron beam from the first path travels later than the spin-polarized electron beam from the second path simply needs to be obtained, and a state in which the spin-polarized electron beam from the first path travels earlier than the spin-polarized electron beam from the second path is not necessary. That is, the second delay device is not a mandatory element.

(7) A majority of samples decelerates the traveling speed of the spin-polarized electron beam. The second delay device is not necessary for measuring speed deceleration as aforementioned. The second delay device is not necessary so long as a sample which accelerates the traveling speed is not measured.

According to the device disclosed herein, coherence of a spin-polarized electron beam can be measured, and an interaction between the spin-polarized electron beam and a sample can be measured.

DESCRIPTION OF EMBODIMENTS

Some of technical features of embodiments described hereinbelow will be listed.

A coherence measuring device may be incorporated in an electron microscope.

The coherence measuring device may measure a rotation angle by which a sample rotates a spin direction of a spin-polarized electron beam.

The coherence measuring device may measure a ratio of electrons of which spin directions are inverted by a sample.

The coherence measuring device may measure a change in a traveling speed of the spin-polarized electron beam caused by a sample.

First Embodiment

Figure 1:
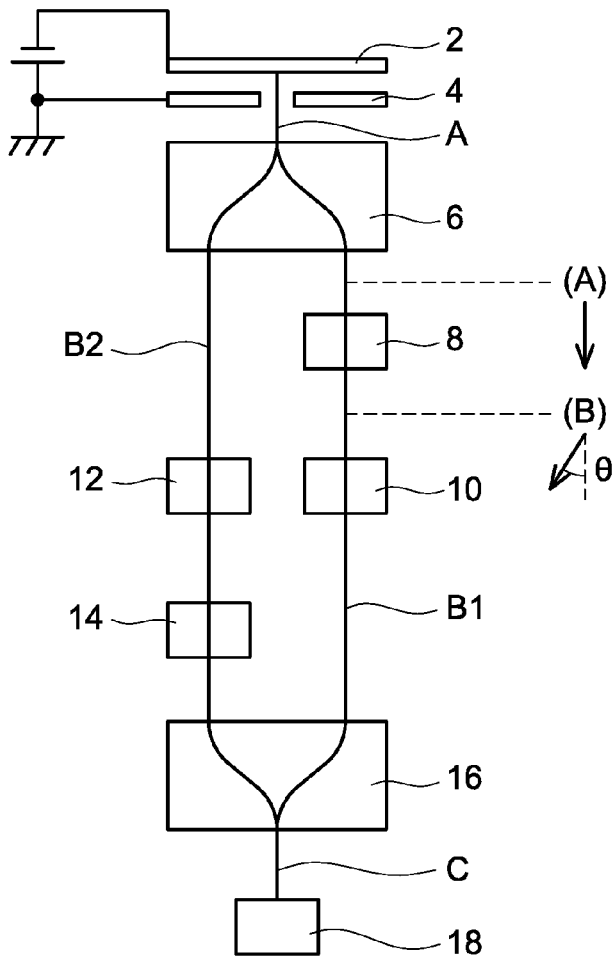
FIG. 1 illustrates a configuration of a coherence measuring device according to a first embodiment.

FIG. 1 illustrates a coherence measuring device according to the first embodiment. Reference numeral 2 indicates a semiconductor photocathode, and when a circular polarized laser beam strikes an upper surface of the semiconductor photocathode, the semiconductor photocathode emits a spin-polarized electron beam from its lower surface. The spin-polarized electron beam herein is an electron beam in which, when a number of up-spin electrons and a number of down-spin electrons are compared, one is significantly superior to the other one, and its electron spin direction is polarized. Details for a device that emits spin-polarized electron beam are disclosed in International Publication No. WO 2011/122171 and Japanese Patent Application Publication No. 2007-258119, of which overlapping description will be omitted.

The spin-polarized electron beam emitted from the lower surface of the semiconductor photocathode 2 is accelerated by an anode electrode 4, and travels downward along a path indicated by reference numeral A. It is possible to switch between exploiting a spin-polarized electron beam with its majority of electrons being spin-oriented along a traveling direction, and exploiting a spin-polarized electron beam with its majority of electrons being spin-oriented along a reverse direction to the traveling direction, by switching polarization directions of the circular polarized laser irradiated to the semiconductor photocathode 2.

Reference numeral 6 indicates a splitter that splits a traveling path of the spin-polarized electron beam traveling downward along the path A into two paths and bends the split two paths such that those paths become parallel. As a result of the spin-polarized electron beam passing through the splitter 6, the spin-polarized electron beam is split into the spin-polarized electron beam traveling along a first path B1 and the spin-polarized electron beam traveling along a second path B2.

On the first path B1, a spin direction rotator 8 and a first delay device 10 are disposed. (A) in FIG. 1 exemplifies a spin direction of the spin-polarized electron beam before entering into the spin direction rotator 8, and indicates a spin direction of the down spin spin-polarized electron beam. (B) in FIG. 1 exemplifies a spin direction after being rotated by θ with the spin direction rotator 8. The first delay device 10 delays the spin-polarized electron beam traveling along the first path B1. For example, at time T1+Δt1, the first delay device 10 emits the electrons, that entered therein at time T1. This indicates that Δt1 is time delayed (delay time).

On the second path B2, a second delay device 12 and a sample stage 14 are disposed. The second delay device 12 delays the spin-polarized electron beam traveling along the second path B2. For example, at time T2+Δt2, the second delay device 12 emits the electrons, that entered therein at time T2. This indicates that Δt2 is delay time.

A sample is set on the sample stage 14. The sample stage 14 is transparent to the spin-polarized electron beam. The sample is so thin that the sample allows the spin-polarized electron beam to pass therethrough. However, the spin direction of the spin-polarized electron beam may be rotated, or the spin direction of some of the electrons in the spin-polarized electron beam may be inverted by an interaction between the electrons and the sample. Depending on samples, a certain sample may cause a traveling speed of the electrons to be changed by the electrons passing through the certain sample. Alternatively, a speed at which the up-spin electrons pass through a sample and a speed at which the down-spin electrons pass through the sample may differ in a sample.

Reference numeral 16 is a biprism which superposes the spin-polarized electron beam that has traveled along the first path B1 and the spin-polarized electron beam that has traveled along the second path B2.

Reference numeral 18 is a super-high sensitivity CCD camera, and has a large number of image cells, each cell outputting a corresponding voltage in proportion to an intensity of the electron beam arriving at each cell. A distribution of the voltages outputted by the respective cells indicates an intensity distribution of the electron beam arriving at an imaging surface. The CCD camera 18 stores the intensity distribution of the electron beam arriving at the imaging surface.

A method on how to use the measuring device of FIG. 1 will be described.

Firstly, a condition is set where the rotation angle θ by the spin direction rotator 8=zero; the delay time Δt1 by the first delay device 10=zero; the delay time Δt2 by the second delay device 12=zero; and no sample is set on the sample stage 14. In this case, the CCD camera 18 captures a clear interference fringe.

Next, a sample is set on the sample stage 14. Then, the interaction between the electrons and the sample causes the spin direction of the spin-polarized electron beam to be rotated, and a time difference is generated between the electron beam from the first path B1 and the electron beam from the second path B2. With the spin-polarized electron beam, a clear interference fringe appears when the spin directions of the two spin-polarized electron beams superposed by the biprism 16 match, and the visibility of the interference fringe decreases when the spin directions become mismatched. Further, a clearer interference fringe appears for the two electron beams simultaneously captured by the CCD camera 18 when there is a smaller time difference in the timings when they were emitted from the semiconductor photocathode 2, and if the time difference is equal to or longer than the coherence time, the interference fringe disappears. Due to this, the visibility of the interference fringe captured by the CCD camera 18 decreases if a sample is set on the sample stage 14.

Figure 2:
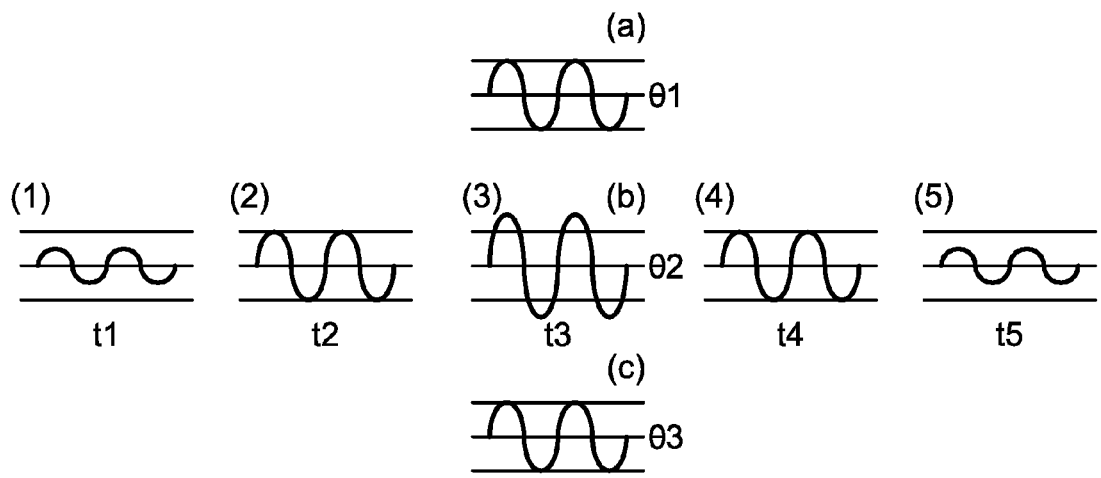
FIG. 2 illustrates interference fringes observed by the coherence measuring device.

After setting the sample on the sample stage 14, the visibility of the interference fringe is measured while changing the rotation angle θ by the spin direction rotator 8. In this case, the visibility of the interference fringe is greatest when a relation "the rotation angle θ by the spin direction rotator $\theta$=a rotation angle of the spin direction by the sample" is established, and the visibility of the interference fringe decreases as the rotation angle $\theta$ by the spin direction rotator 8 deviates from the aforementioned relation. (a), (b), and (c) in FIG. 2 indicate relationships between the rotation angle $\theta$ by the spin direction rotator 8 and the visibility of the interference fringe, and it is indicated in this case that the visibility of the interference fringe is the greatest when the rotation angle by the spin direction rotator 8 is $\theta 2$, and at the deviated rotation angles $\theta 1$ and $\theta 3$, the visibility of interference fringe is decreased.

As a result of this, it is identified that the interaction between the sample and the spin-polarized electron beam caused the spin direction to rotate by $\theta 2$.

Next, the visibility of the interference fringe is measured by setting the delay time $\Delta t2$ by the second delay device 12=zero, and changing the delay time $\Delta t1$ by the first delay device 10. In this case, the visibility of the interference fringe is the greatest when a relation "the delay time $\Delta t1$ by the first delay device 10=a delay time by the sample" is established, and the visibility of the interference fringe decreases as the delay time $\Delta t1$ by the first delay device 10 is deviated from the aforementioned relation. (1) to (5) of FIG. 2 indicate relationships between the delay time $\Delta t1$ by the first delay device 10 and the visibility of the interference fringe, and this case exemplifies a case where the visibility of the interference fringe is the greatest when the delay time $\Delta t1$=t3. (2) and (4) indicate a case where the visibility of the interference fringe takes a predetermined threshold value, and (1) and (5) indicate a case where the visibility of the interference fringe is below the predetermined threshold value. As a result of this, it can be understood that the delay time brought forth by the sample is t3, and the coherence time is (t3−t2) or (t4−t3). The coherence time varies depending on samples. A sample that interacts more intensively with electrons has a shorter coherence time.

As in the above manner, the coherence measuring device of FIG. 1 is configured to measure the rotation angle $\theta 2$ by which the sample rotates the spin direction, the delay time t3 by which the sample delays the traveling speed of the electron beam, and the coherence time after passing through the sample. A coherence length can also be measured from the coherence time and the traveling speed of the electrons.

The above coherence measuring device can also be configured to measure the coherence time of the spin-polarized electron beam emitted from the semiconductor photocathode 2. In this case, the visibility of the interference fringe is measured by not setting any sample, setting the rotation angle $\theta$ by the spin direction rotator 8=zero and the delay time $\Delta t2$ by the second delay device 12=zero, and increasing the delay time $\Delta t1$ by the first delay device 10 from zero. The visibility of the interference fringe is the greatest when the delay time $\Delta t1$=zero, and the visibility of the interference fringe decreases as the first delay time $\Delta t1$ becomes longer. The coherence time can be measured from the first delay time $\Delta t1$ by which the visibility of the interference fringe drops below a predetermined threshold level.

Next, the visibility of the interference fringe is measured by not setting any sample, setting the rotation angle $\theta$ by the spin direction rotator 8=zero and the first delay time $\Delta t1$ by the first delay device 10=zero, and increasing the second delay time $\Delta t2$ by the second delay device 12 from zero. The visibility of the interference fringe is the greatest when the second delay time $\Delta t2$=zero, and the visibility of the interference fringe decreases as the second delay time $\Delta t2$ becomes longer. The coherence time can be measured from the second delay time $\Delta t2$ by which the visibility of the interference fringe drops below a predetermined threshold level.

In the above, $\Delta t1$ and $\Delta t2$ are both measured. Theoretically, the coherence can be known from one of $\Delta t1$ and $\Delta t2$. If one of the first delay device 10 and the second delay device 12 is provided, the coherence can thereby be measured.

Depending on samples, a certain sample may accelerate the spin-polarized electron beam passing therethrough. In this case, the visibility of the interference fringe is measured by setting the first delay time $\Delta t1$ by the first delay device 10=zero, and changing both the rotation angle $\theta$ by the spin direction rotator 8 and the second delay time $\Delta t2$ by the second delay device 12. The visibility of the interference fringe is the greatest when an acceleration effect by the sample is balanced out by a delay effect by the second delay device 12. With the second delay device 12 being provided, it is also possible to conduct measurements when a sample accelerates the spin-polarized electron beam.

A majority of samples decelerates the traveling speed of the electron beam passing therethrough. If it suffices to simply measure a magnitude of this deceleration in the traveling speed, the second delay device 12 is not a mandatory element.

Depending on samples, a certain sample may invert the spin direction of some of the spin-polarized electrons passing therethrough. A ratio of the spin-polarized electrons with the inverted spin direction can be measured from the visibility of the interference fringe when the visibility is the greatest. A sample that interacts with electrons more intensively has a greater rate of inverting the spin direction, which indicates that the sample is not suitable as a material used in a memory. Thus, it becomes possible to acknowledge the characteristic of the sample.

Further, it is also possible to measure a speed at which the up-spin electrons pass through a sample and a speed at which the down-spin electrons pass through the sample by measuring the visibility of the interference fringe while adjusting the delay time and the rotation angle.

Second Embodiment

Figure 3:
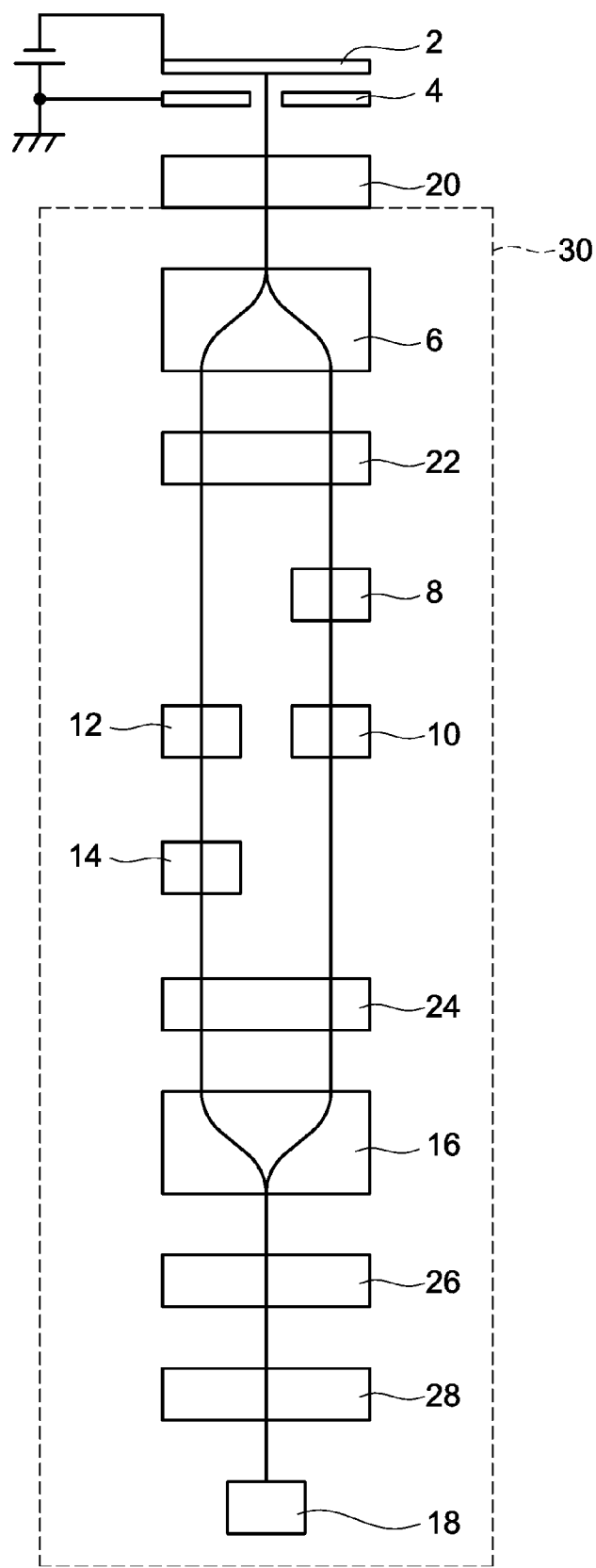
FIG. 3 illustrates a configuration of a coherence measuring device according to a second embodiment.

FIG. 3 illustrates a structure of a device with a coherence measuring device incorporated in a transmission electron microscope, and same descriptions of like components depicted in FIG. 1 will be omitted by using like numerals.

Reference numeral 30 indicates a configuration of the electron microscope but excludes depiction of a generator of the spin-polarized electron beam. Reference numeral 20 indicates a connector device between the spin-polarized electron beam generator and the transmission electron microscope, 22 indicates a condenser lens, 24 indicates a sample lens, 26 indicates an intermediate lens, and 28 indicates a projector lens. Details for these components are disclosed in International Publication No. WO 2011/122171, of which overlapping description will be omitted.

Incorporating the coherence measuring device in the transmission electron microscope enables to measure interaction between a sample and the spin-polarized electron beam for each of micro areas in the sample.

It should be noted that the splitter 6 may be disposed upstream or downstream of the condenser lens 22. Further, the biprism 16 may be disposed between the sample lens 24 and the intermediate lens 26, between the intermediate lens 26 and the projector lens 28, or between the projector lens 28 and the CCD camera 18. The spin direction rotator 8, the first delay device 10, and the second delay device 12 may only have to be placed between the splitter 6 and the biprism 16, and may not be restricted by positional relationships regarding the condenser lens 22, the sample lens 24, the intermediate lens 26, and the projector lens 28. The embodiment simply needs to have a relationship in which the splitter is disposed upstream of the sample stage, the biprism is disposed downstream of the sample lens, and both the spin-polarized electron beam traveling on the first path and the spin-polarized electron beam traveling on the second path pass through the sample lens.

In the present embodiment, the coherence measuring device is incorporated in the transmission electron microscope (TEM), however, the coherence measuring device may be incorporated in all kinds of devices using electron beam such as SEM, LEEM, and RHEED.

The phenomena obtained by the coherence measuring device of FIG. 1 will be described using formulas.

The up-spin spin-polarized electrons will be indicated by Formula 1, and the down-spin spin-polarized electrons will be indicated by Formula 2.

$$|\uparrow\rangle = \begin{pmatrix} 1 \\ 0 \end{pmatrix} \quad \text{[Formula 1]}$$

$$|\downarrow\rangle = \begin{pmatrix} 0 \\ 1 \end{pmatrix} \quad \text{[Formula 2]}$$

The spin direction rotator applies an operation indicated by Formula 3. θ is an angle indicating a spin direction in a plane along electron path, and φ is an angle indicating a spin direction in a plane orthogonal to the electron path.

$$R_{spin}(\theta,\phi) = \begin{pmatrix} \cos\frac{\theta}{2} & -\sin\frac{\theta}{2} \\ e^{-i\phi}\sin\frac{\theta}{2} & e^{-i\phi}\cos\frac{\theta}{2} \end{pmatrix} \quad \text{[Formula 3]}$$

$$\theta = \mu_B B_\perp \tau/\hbar, \quad \phi = \mu_B B_\parallel \tau/\hbar$$

B: Magnetic field, $\mu_B$: Bohr magneton
τ: interaction time

The first delay device applies an operation indicated by Formula 4, and the second delay device applies an operation indicated by Formula 5.

$$D(\delta_R) = \exp(-i\delta_R)\begin{pmatrix} 1 & 0 \\ 0 & 1 \end{pmatrix} \quad \text{[Formula 4]}$$

$$D(\delta_L) = \exp(-i\delta_L)\begin{pmatrix} 1 & 0 \\ 0 & 1 \end{pmatrix} \quad \text{[Formula 5]}$$

If the semiconductor photocathode 2 emits the up-spin electrons, a wave equation of the electron beam entering the biprism from the first path is Formula 6, and a wave equation of the electron beam entering the biprism from the second path is Formula 7. T in Formula 7 indicates the interaction the sample brings forth for the electron beam.

$$|\Psi_R\rangle = D(\delta_R) \cdot R_{spin}(\theta,\phi) \cdot |\uparrow\rangle \quad \text{[Formula 6]}$$

$$|\Psi_L\rangle = T \cdot D(\delta_L) \cdot |\uparrow\rangle \quad \text{[Formula 7]}$$

The intensity of the electron beams superposed by the biprism is indicated by Formula 8.

$$(\langle\Psi_R| + \langle\Psi_L|)(|\Psi_L\rangle + |\Psi_R\rangle) = \quad \text{[Formula 8]}$$

$$\langle\Psi_R|\Psi_R\rangle + \langle\Psi_L|\Psi_L\rangle + \langle\Psi_L|\Psi_R\rangle + \langle\Psi_R|\Psi_L\rangle =$$

$$\frac{1}{2} + \frac{1}{2}\langle\uparrow|T^\dagger T|\uparrow\rangle + \frac{1}{2}\langle\uparrow|T^\dagger D^\dagger(\delta_L)D(\delta_R)R_{spin}(\theta,\phi)|\uparrow\rangle +$$

$$\frac{1}{2}\langle\uparrow|R_{spin}(\theta,\phi)^\dagger D^\dagger(\delta_R)D(\delta_L)T|\uparrow\rangle$$

T=1 is assumed when no sample is inserted.

In this case, a formula indicating the interference fringe is Formula 9, and the coherence of the spin-polarized electron beam itself can be measured from a relationship between the delay time of the delay device and the visibility of the interference fringe.

Formula 10 becomes applicable if spin flop is generated in the sample, and a formula indicating the interference fringe is Formula 11. An effect of the spin flop can be measured by measuring the visibility of the interference fringe while changing the rotation angle by the spin direction rotator.

$$= 1 + \cos(\delta_R - \delta_L)\cos\left(\frac{\mu_B B \tau}{2\hbar}\right) \quad \text{[Formula 9]}$$

$$T = \begin{pmatrix} f & -g \\ g & f \end{pmatrix} \quad \text{[Formula 10]}$$

$$1 + \frac{1}{2}\langle\uparrow|T^\dagger D(\delta_R - \delta_L)R_{spin}(\theta,\phi)|\uparrow\rangle + \quad \text{[Formula 11]}$$

$$\frac{1}{2}\langle\uparrow|R_{spin}(\theta,\phi)^\dagger D(-\delta_R + \delta_L)T|\uparrow\rangle =$$

$$1 + \frac{1}{2}e^{-i(\delta_R-\delta_L)}\left[f\cos\frac{\theta}{2} + g\sin\frac{\theta}{2}\right] +$$

$$\frac{1}{2}e^{i(\delta_R-\delta_L)}\left[f\cos\frac{\theta}{2} + g\sin\frac{\theta}{2}\right] =$$

$$1 + \cos(\delta_R - \delta_L)\left[f\cos\frac{\theta}{2} + g\sin\frac{\theta}{2}\right]$$

Depending on samples, a certain sample may exhibit different interactions for the up-spin electrons and the down-spin electrons. The interaction by the sample at such occasion is Formula 12.

In this case, the interference fringe by the up-spin electrons is Formula 13, and the interference fringe by the down-spin electrons is Formula 14. Formula 15 is obtained by Formula 13 and Formula 14. A difference in inner potential in the sample can be identified based on Formula 15 and the measured results.

$$T = \begin{pmatrix} T_{up} & 0 \\ 0 & T_{down} \end{pmatrix} = \begin{pmatrix} \exp(ik_\uparrow x) & 0 \\ 0 & \exp(ik_\downarrow x) \end{pmatrix} \approx \quad \text{[Formula 12]}$$

$$\begin{pmatrix} \exp\left(i\frac{\sqrt{2m_e(E_k - V_\uparrow)}}{\hbar}x\right) & 0 \\ 0 & \exp\left(i\frac{\sqrt{2m_e(E_k - V_\downarrow)}}{\hbar}x\right) \end{pmatrix}$$

$$1 + \frac{1}{2}\langle\uparrow|T^\dagger D(\delta_R - \delta_L)R_{spin}(\theta,\phi)|\uparrow\rangle + \quad \text{[Formula 13]}$$

$$\frac{1}{2}\langle\uparrow|R_{spin}(\theta,\phi)^\dagger D(-\delta_R + \delta_L)T|\uparrow\rangle =$$

$$1 + \cos(\delta_R - \delta_L - k_\uparrow x)\cos\frac{\theta}{2}$$

-continued $$1 + \frac{1}{2}\langle\downarrow\uparrow|T^\dagger D(\delta_R - \delta_L)R_{spin}(\theta, \phi)|\downarrow\rangle +$$ [Formula 14]

$$\frac{1}{2}\langle\downarrow|R_{spin}(\theta, \phi)^\dagger D(-\delta_R + \delta_L)T|\downarrow\rangle =$$

$$1 + \cos(\delta_R - \delta_L - k_\downarrow x)\cos\frac{\theta}{2}$$

$$(k_\uparrow - k_\downarrow)x = \left(\frac{\sqrt{2m(E_k - V_\uparrow)}}{\hbar} - \frac{\sqrt{2m(E_k - V_\uparrow)}}{\hbar}\right)x \cong$$ [Formula 15]

$$\frac{(V_\downarrow - V_\uparrow)}{2E_k}\frac{\sqrt{2mE_k}}{\hbar}x$$

Specific examples of the present invention have been described in detail, however, these are mere exemplary indications and thus do not limit the scope of the claims. The art described in the claims include modifications and variations of the specific examples presented above. Technical features described in the description and the drawings may technically be useful alone or in various combinations, and are not limited to the combinations as originally claimed. Further, the art described in the description and the drawings may concurrently achieve a plurality of aims, and technical significance thereof resides in achieving any one of such aims.

The invention claimed is:

1. A coherence measuring device for a spin-polarized electron beam, the device comprising:
   a semiconductor photocathode configured to emit a spin-polarized electron beam of which spin direction is polarized;
   a splitter configured to split a path of the spin-polarized electron beam emitted from the semiconductor photocathode into two paths;
   a spin direction rotator and a first delay device that are disposed on a first path which is one of the split two paths split by the splitter;
   a sample stage disposed on a second path which is another of the two paths split by the splitter;
   a biprism configured to superpose spin-polarized electron beams split into the first path and the second path; and
   an intensity distribution measuring device configured to measure an intensity distribution of the spin-polarized electron beams superposed by the biprism.

2. The coherence measuring device according to claim 1, further comprising
   a second delay device disposed on the second path.

3. A method of measuring a change a sample imparts to a traveling speed of a spin-polarized electron beam using the coherence measuring device according to claim 2, the method comprising:
   measuring a relation between a time difference between a delay time by the first delay device and another delay time by the second delay device and a visibility of an interference fringe obtained when the intensity distribution is measured; and
   specifying a time difference with which the interference fringe is clearest.

4. An electron microscope in which the coherence measuring device according to claim 2 is incorporated, wherein the semiconductor photocathode is further configured to function as an electron source for the electron microscope.

5. An electron microscope in which the coherence measuring device according to claim 2 is incorporated, wherein both the spin-polarized electron beam traveling on the first path and the spin-polarized electron beam traveling on the second path pass through a sample lens of the electron microscope.

6. The electron microscope according to claim 5, wherein the biprism is disposed downstream of the sample lens.

7. The electron microscope according to claim 6, wherein the splitter is disposed upstream of the sample stage.

8. A method of measuring a rotation angle by which a sample rotates a spin direction of a spin-polarized electron beam using the coherence measuring device according to claim 2, the method comprising:
   measuring a relation between the rotation angle by the spin direction rotator and a visibility of an interference fringe obtained when the intensity distribution is measured; and
   specifying a rotation angle with which the interference fringe is clearest.

9. An electron microscope in which the coherence measuring device according to claim 1 is incorporated, wherein the semiconductor photocathode is further configured to function as an electron source for the electron microscope.

10. An electron microscope in which the coherence measuring device according to claim 1 is incorporated, wherein both the spin-polarized electron beam traveling on the first path and the spin-polarized electron beam traveling on the second path pass through a sample lens of the electron microscope.

11. The electron microscope according to claim 10, wherein the biprism is disposed downstream of the sample lens.

12. The electron microscope according to claim 11, wherein the splitter is disposed upstream of the sample stage.

13. A method of measuring a rotation angle by which a sample rotates a spin direction of a spin-polarized electron beam using the coherence measuring device according to claim 1, the method comprising:
   measuring a relation between the rotation angle by the spin direction rotator and a visibility of an interference fringe obtained when the intensity distribution is measured; and
   specifying a rotation angle with which the interference fringe is clearest.

* * * * *